United States Patent [19]
Meyer

[11] Patent Number: 5,478,324
[45] Date of Patent: Dec. 26, 1995

[54] PREFILLED SYRINGE FOR STORING AND FOR TRANSFER OF LIQUID AND STERILE MEDICINAL SUBSTANCES

[75] Inventor: Gabriel Meyer, Dully, Switzerland

[73] Assignee: Medicorp Holding S.A., Switzerland

[21] Appl. No.: 318,705

[22] PCT Filed: Feb. 18, 1994

[86] PCT No.: PCT/IB94/00016

§ 371 Date: Oct. 12, 1994

§ 102(e) Date: Oct. 12, 1994

[87] PCT Pub. No.: WO94/19034

PCT Pub. Date: Sep. 1, 1994

[30] Foreign Application Priority Data

Feb. 19, 1993 [FR] France ................ 93 01998

[51] Int. Cl.⁶ .................................................. A61M 5/00
[52] U.S. Cl. ..................... 604/203; 604/218; 604/232
[58] Field of Search ............................ 604/218, 232, 604/236, 237, 200, 201, 202, 203, 187, 184, 231

[56] References Cited

U.S. PATENT DOCUMENTS

| | | |
|---|---|---|
| 2,574,339 | 11/1951 | Lackhart . |
| 3,563,415 | 2/1971 | Ogle . |
| 3,722,512 | 3/1973 | Hein et al. . |
| 3,841,329 | 10/1975 | Killinger . |
| 3,941,131 | 3/1976 | Ogle ................................ 604/203 |
| 3,965,898 | 6/1976 | Cloyd ............................... 604/203 |
| 3,980,083 | 9/1976 | Elliott ........................... 604/203 X |
| 3,994,296 | 11/1976 | Cloyd ............................... 604/203 |
| 4,020,831 | 5/1977 | Adler ............................ 604/231 X |
| 4,078,565 | 3/1978 | Genese .......................... 604/218 X |
| 5,084,018 | 1/1992 | Tsao . |
| 5,098,403 | 3/1992 | Sampson . |
| 5,114,410 | 5/1992 | Caralt Batlle . |

FOREIGN PATENT DOCUMENTS

| | | |
|---|---|---|
| 0111796 | 12/1983 | European Pat. Off. . |
| 0146558 | 5/1984 | European Pat. Off. . |
| 2300578 | 9/1976 | France . |
| 2667249 | 10/1990 | France . |
| 2262706 | 2/1972 | Germany . |
| 2023772 | 2/1992 | Spain . |
| 1159663 | 7/1969 | United Kingdom . |
| 87/06141 | 10/1987 | WIPO . |
| 91/00215 | 1/1991 | WIPO . |
| 92/18178 | 10/1992 | WIPO . |
| 92/22338 | 12/1992 | WIPO . |

OTHER PUBLICATIONS

Vol. 49, Aug. 1992, Am. Hosp. Pharm. 1851; letter dated Oct. 26, 1992 of Suzan A. Coutrell, Director, ASHP Home Care and Management Department of Edmund M. Fry, PDA Executive Vice President.

*Primary Examiner*—John D. Yasko
*Attorney, Agent, or Firm*—Davis, Bujold & Streck

[57] ABSTRACT

A syringe (10) comprising a glass container (11) having a closed bottom end and containing a liquid drug (12). The container is sealed by an axially slidable plug/plunger/valve assembly (17) provided with a slot (19) defined by two mutually engaged sealing lips and coupled to a rod (22) centered within a body (13) coupled to the container (11). The rod comprises an axial channel (23) with one end cut off along a plane perpendicular to its axis to enable a needle (15) to be operably connected to the contents (12) of the container (11) by parting the lips of the slot (19). Said rod is further provided with an assembly for coupling same to said plug (17) when the container has been driven into the body (13).

11 Claims, 10 Drawing Sheets

PREFILLED SYRINGE FOR STORING AND FOR TRANSFER OF LIQUID AND STERILE MEDICINAL SUBSTANCES

This application is a 371 of PCT/IB94/00016 filed Feb. 18, 1994.

The present invention relates to a prefilled syringe for storing and for transfer of a liquid and sterile medicinal substances, having a rigid reservoir made of glass, with a closed bottom and closed at its opposite open end by means of a stopper—piston—valve, which is axially slidable, the reservoir being axially movable within a cylindrical body and has a shaft connected to the stopper—piston—valve and is provided with an axial conduit adapted to communicate with a needle fixed to the end of the body, opposite to the reservoir.

There are a variety of devices of this type, which have as object to contain a liquid and sterile substance intended to be transferred by direct injection to a patient or to another receiving instrument.

The prefilled syringe described in U.S. Pat. No. 2,574,339 comprises a central double needle, the end of which perforates a piston closing off a container. This syringe has the advantage of permitting the transfer of a liquid contained in the container by exerting pressure on the container without having to apply other manipulations in order to activate the syringe. This pressure effect perforates the piston by the central needle in order to permit the flow of the solution along this needle. The main disadvantage of this syringe is that it is impossible to use it for withdrawing a patient's blood into the container, from the time of direct injection in order to obtain a "vein" test or a mixture obtained after transfusion to a different device. Added to this disadvantage, are the costly manufacture of a double needle having bevellings at both ends, the perforation by this needle of the central part of the piston, which generates undesirable particles which are impossible to eliminate, and finally the fact that the injection needle is irreversibly attached to the body of the syringe, and cannot be withdrawn away into the body of the syringe after use.

The syringe has to be closed off as before in order to protect it after use, which fact at present represents a major risk of accidental contamination to a person due to being pricked by a soiled needle. The Food and Drug Administration (FDA) as well as the American Society of Hospital Pharmacists (ASHP) encourage the design of systems provided with a needle for the preparation of injectionable solutions for injecting a solution to a patient and the retraction of such a needle into the needle device after use (Vol. 49, Aug. 1992 Am. Hosp. Pharm. 1851; Letter dated Oct. 26, 1992 of Suzan A. Coutrell, Director, ASHP Home Care and Management Department to Edmund M. Fry, PDA Executive Vice President). Furthermore, this needle does not provide means to prevent its re-use. This applies both to the proximal part as well as to the distal part, due to the fact that means for fixing the container to the body is not provided. This syringe also is not provided with means to permit the maintainance of sterility of the piston surface before being perforated by the needle and of the needle itself.

Patent WO-A-92/18178 describes a syringe of which the stopper is perforated by a needle, which causes a considerable risk of injecting solid particles into a patient's blood stream.

U.S. Pat. No. A 3,841,329 describes a needle in which the stopper serves both as piston as well as a valve and is pierced. The piercing is, however, by way of a membrane of significant thickness, so that the slit made must open under pressure exerted by the liquid contained in the reservoir. For this reason this system results in a lack of tightness, which in turn implies that the stopper— piston—valve of necessity must be connected to the shaft for transferring prior to its hermetical positioning in the reservoir and that it is impossible to achieve suction, particularly for effecting the "vein" test. The lack of tightness is the most serious consequence, namely the loss of sterility to the charge in the needle.

The syringe described in U.S. Pat. No. 1,159,663 similarly provides a double needle. It has a screw-coupling between the piston and a central cylinder located inside the body and surrounding the double needle. This construction does not only not solve the problem of possible suction on completion of use but it also brings about additional disadvantages. The container has to be turned in order to activate the system, which complicates the manipulation and requires that frictional forces of the piston against the glass inner sides will always be greater than the screwing forces. However, it is expedient to control several delicate manufacturing paremeters with consequent heavy losses. The manufacture of the body is not by way of moulding. It is in effect impossible to obtain rapid cycles of production by reason of the impossibility to be able to cool the body interior. Furthermore, the air in the syringe may be evacuated from the time of conditioning by the piston part of the container, which, besides, presents a disadvantage during manufacture of the container having advantageously a fire proof floor. This latter requirement contains a certain quantity of gas so that it would be necessary to purge it before proceeding with a direct injection to a patient.

In order to respond to the requirements of the pharmaceutical industry, a prefilled syringe may not have such disadvantages. It therefore would be necessary to develop means to permit a condition in a liquid substance in a glass container with a fire proof floor, which is totally free from gas in order to avoid the step of purging and to enhance the conservation of solutions not supporting the presence of oxygen or, when the "vein" test is not required as this may be the case in certain countries, for subcutaneous injections in small quantities. Furthermore it is impossible to eliminate fully the oxygen itself by way of a meticulous gassing by means of a neutral gas, such as nitrogen or carbonic gas, as long as there exists a gaseous residue in the reservoir.

The devices proposed in U.S. Pat. Nos. 3,563,415 and 3,722,512 provide the omission of the total presence of gas surpassing the liquid solution by having a long piston allowing for a central channel not closed off by the medical substance to be conserved. This construction does not require piercing of the container in a tight manner after conditioning of the solution with a view to providing a final sterilization by way of an autoclave, such as the registration authorities actually require for all liquid substances to endure heat treatment.

The proposed devices in the European patent published under No. 0 111 796 and 0 146 558 describe similar systems, which do not resolve problems posed by the presence of gas in a container closed at the bottom, nor that of autoclave sterilization of the container of the container in a manner independent of the body. All of these devices allow the omission of the perforation of the piston by having a piston system playing the role of a valve in co-operating with an appropriate form of container neck. This construction requires the user to direct the syringe upwards and to push the container through a precise length to bring the radial channel of the piercer into communication with the larger diameter of the container so to purge it initially of air without projecting liquid to the exterior. These manipulations are delicate and are incompatible with a modem device for instantaneous use and without risk of error. Such devices must of necessity be used together with accessories, which allow the limitation of the activation and to purge in a precise manner. Furthermore, these systems cannot be used in an easy way for transferring the contents to a bottle containing a different substance and they do not permit complete resuction of the mixture constituted within the container without sucking a quantity of gas. Of less importance it is that afterwards it has to be purged along a central channel, which will of necessity contain a certain quantity of solution. Such devices should be capable to integrally withdraw the mixture in a controlled manner in order to achieve an injection without the neccesity to purge.

The syringe proposed in the German patent No. 22 62 706 does not solve the problems as stated above and has the same disadvantages as those mentioned in relation to U.S. Pat. No. 1,159,663.

It is therefore to be concluded that all the former known devices have a number of disadvantages and some solve part of the disadvantages and are based on constructions, which present additional disadvantages starting with the simple non-acceptable fact of the medical risk of injecting air into a patient or the impossibility to protect the sterile solution adequately.

Furthermore, all of these known devices do not allow the prefilled syringe to be connected in a stable way to a normal bottle containing a dry substance to be mixed with a solvent contained in these syringes, nor to protect the needle from the time of perforation of the plug closing off the bottle containing the other substances in order to preserve the bevelling so as to proceed to a final injection of the mixture constituted thereby and so that the procedures correspond to recent recommendations mentioned of the FDA and the ASHP. Finally these wellknown syringes do not permit reconstitution of pharmacologically strongly activated substances, such as anti-cancer and antibiotic substances of which some may dislodge gas from the time of reconstitution. It is in effect imperative for such substances that the device for storing and transferring be equipped with means of permitting a tight connection with the bottle containing substances and that, from the time of disconnection of the device for transfer, it will not produce any nebulization or spray. In certain instances it is necessary to puncture the mixture contained in at least two bottles inside the syringe in order to adapt the set-up corresponding to the patient's weight, age and intensity of treatment required. All such operations should be performed without any danger of contamination of the person in attendance or to his environment and without contamination of the mixture by the ambient environment or by any other substances.

When the syringes are already equipped with an injection needle, this needle must be protected from the environment and from all other soiling in order to remain intact until the moment of injection and, above all, in order to avoid an accidental pricking from the time of preparation, where a needle ought not to be utilized, according to recent recommendations by the FDA and the ASHP. Furthermore means have to be provided routinely in all operations of transfer to avoid an accidental pricking as well as after use of the syringe or an injection.

It will be noted that the devices proposed cannot be used as sterile opthalmic drop distributors or as nasal sprays by reason of the absence of means of obturation of the container piston on the completion of use, for means are not provided that the piston opens at a determined threshold pressure to obtain a nebulization which may not be obtained by other than a pressure threshold. Furthermore they do not allow the administration of successive precise dosages, for they do not have means to routinely equip these devices with limitators. Furthermore when these ophtalmic and nasal devices are used for multiple dosages, no means is provided to inhibit the passing over of bacteria into the applicator ferrule.

The claims made by the patent published under no. WO 91/00215 provides for a device permitting protection of the needle from the time of transfer of a solution into a normal bottle. However, this device is independent from the kind where the state of being disposable of such a device is not guaranteed at the moment of transfer. Such means must imperatively be part of the device for storing and transferring ready for use liquid in order to meet the requirement of the FDA and ASHP.

Devices provided for the protection of the needle after use by retraction of the needle into a protection body or by the advance of a protection over the needle, are proposed in several patents. All of these constructional proposals require syringes obturated at their distal end by a piston, the shaft of which activates its sliding. No means of this type have been provided in a prefilled device allowing for a container closed at the bottom, notably in devices which are the subject of the U.S. Pat. No. 5,098,403; U.S. Pat. No. 5,084,018; F 2 667 249; ES 2 023 772 and U.S. Pat. No. 5,114,410.

The present invention proposes to overcome all such disadvantages and those mentioned above in proposing a syringe, which offers a solution to the complexity of problems contained in known syringes and which meets the most recent requirements for storing and transfer of a sterile liquid solutions for all types of applications, such as the direct injection to a patient by means of a needle, the sterile nasal spray and the distribution of sterile ophthalmic drops.

This object is achieved by a syringe according to the invention, characterized in that the stopper—piston—valve has a central zone provided with an opening in the form of a slot defined by two tightly fitting lips, and in that the shaft is provided with means to be firmly connected to the stopper—piston—valve, when the reservoir is axially displaced within the cylindrical body, and in that the axial conduit is provided with a cutting end along a substantially perpendicular plane to its axis adapted to separate the lips and to open the slot for placing the axial conduit into communication with the reservoir.

According to one advantageous embodiment the shaft is connected to a flange adapted to give support to the distal end of the cylindrical body.

In a different preferred form, the means for connecting the shaft includes a clamping block provided with a peripheral neck is defined by a first and second shoulder provided on both sides at the neck, and an annular protuberance provided in a central zone of the stopper—piston—valve the protuberance being adapted to move during charging of the syringe in the neck such to define a firm connection between the shaft and the stopper—piston—valve with a tight connection formed as antiseptic barrier between both these elements.

In a preferred embodiment the first shoulder is adapted to offer less resistance to the compression of the protuberance than that of the second shoulder.

Preferably the first shoulder has a smaller dimension than of the second shoulder.

In a preferred embodiment of manufacture the stopper—piston—valve has at least one shoulder adapted to give support during storage to an internal shoulder of the reservoir.

Furthermore, the reservoir advantageously has an exterior shoulder arranged to co-operate with the neck provided at the free end of the body. Similarly it allows for an interior shoulder located to co-operate with an enlargement located at the base of the shaft on completion of use.

The present invention and its main advantages will be better understood with reference to a description of examples of embodiments illustrated in the annexed drawings, in which.

Figures 1, 2:
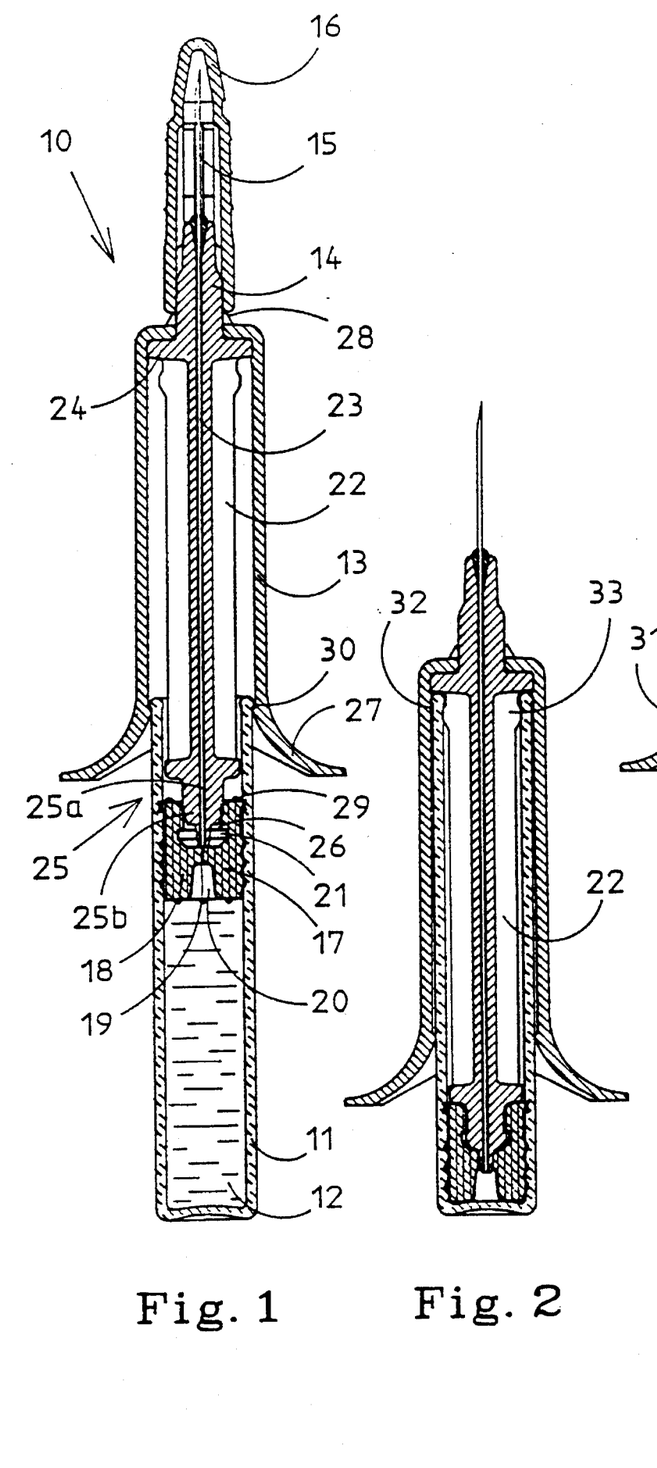
FIG. 1 shows a sectional view of a prefilled syringe according to the invention, shown in the storage position.
FIG. 2 shows the syringe of FIG. 1 on completion of the injection phase.

Referring to FIG. 1, a refillable syringe 10 has a rigid reservoir 11, preferably made of glass in order to be able to sustain the thermic constraints of sterilization by way of an autoclave or the like, the reservoir being filled with an injectionable medicinal substance 12 and carrying a needle 15 protected by a hood 16 in the front opening of a body 13 whose front end is equipped with a ferrule 14. The reservoir is pierceable by a stopper—piston—valve 17 having a sectional profile in the shape of an H and is provided with a central zone 18 defining a slot 19, which connects two grooves, respectively an upstream groove 20 and a downstream groove 21. The upstream groove is disposed at the side of the reservoir and the downstream groove is disposed on the side of the body 13.

A rigid shaft 22 is mounted within the body, in which shaft is provided an axial conduit 23. In the construction as shown, the shaft 22 is connected to a flange 24, which in turn is connected to the ferrule 14. This shaft is closed off at its end opposite to the ferrule 14 by a clamping block 25 arranged so as to be engaged in the groove 21 of the of the stopper—piston—valve 17. In this embodiment likewise the axial conduit 23 is located in the extension of the needle 15 and is provided by way of a channel inside the shaft 22. At its end the clamping block 25 has a tip 26 surrounding the end of the shaft 22 or constituted by this end tip, this tip being adapted to penetrate the slot 19 for opening it to separate the lips, which define it at the moment when the clamping block is partially engaged in the groove below the stopper—piston—valve.

The body 13 furthermore is provided with ribs 27, preferably made integrally with this body by an injection moulding process of synthetic plastics material. It is to be noted that the needle 15 and the shaft should be made integrally, but for reasons of production costs, it is preferred that a standard needle be used and this be fixed by attachment or by casting in a mould or moulding to the shaft at the end of the ferrule 14. Finally connection arms 28 connect the hood 16 to the body 13.

In the form shown the clamping body 25 has a large part 25a with a diameter, which is substantially equal to the interior diameter of the body and a narrow part 25b, which corresponds to the downstream groove 21. The larger part centres the shaft, and the narrow part provides the coupling of the stopper—piston—valve 17 to the shaft 22. During storage the stopper—piston—valve is coupled to the shaft by friction in order to ensure the maintenance of sterility at the level of the groove 21. It plays the role of a stopper and close off the reservoir 11 during the charging phase. From the moment on when coupling of the stopper—piston—valve and the shaft is completely achieved, this part turns into a piston, which compresses the medicinal liquid 12 the slot 19, which is held open by the tip 26, into the axial conduit 23 in the direction of the needle 25.

It has to be mentioned that the slot 19 is not perforated by the tip 26, but that the latter is pre-cut, that is to say, made during manufacture of the stopper—piston—valve. This tip 26 separates the lips of the slot 19 by resilient deformation. Its opening is achieved without lifting of the material, a fact which omits the risk of injecting particles into a patient's body. This slot opens when the tip is engaged therein and closes off when it is retracted. For this reason it fulfils the function of a valve.

The downstream groove 21 is surrounded by a shoulder 29, which forms a frictional zone with a narrow part 25b of the clamping block 25 forming the top of the shaft 22. This frictional zone provides the bacterial tightness of the lower zone of the downstream groove 21 during storage of the syringe.

In this fashion the slot remains sterile during storage. The flange 24 and the ferrule 14 constitute another bacterial barrier. This barrier is completed by the hood, the base of which is frictionally fixed on the ferrule 14.

The open end of the reservoir provides an external shoulder 30, which cooperates with an associated neck 31, provided on the free end of the body 13 in order to provide an irreversible coupling of the prefilled reservoir and provided with its stopper—piston—valve on its body.

The syringe shown is ready for use and does not contain any gas, which ensures that no purging operation is required. For this reason the needle remains dry and uncontaminated by a flow of medicinal substance, which is transported by the gas at the moment of degassing of the known syringes at the very moment of injection.

From the time of manufacture of the syringe, the reservoir is subjected to dilution, decontamination by ultrasound, an adequate siliconisation of the internal surfaces and a fixation of the reticulation with heat in order to form a film having ideal properties for sliding. At the same time as the reticulation takes place, the reservoir is depyrogenized. Both these operations, performed at a temperature approaching 300° C. for a period of five minutes, are made possible by the fact that the needle is not fixed by gluing to the reservoir. Subsequently the reservoir is filled and the stopper—piston—valve is fitted. Due to the central slot of the stopper, the positioning shaft of the piston of a gluing device puts the stopper into its place with a central channel, and with accessory means of suction. This hollow shaft supports itself on the slotted central part, it exerts a resilient deformation of the inner sides and the slot becomes an opening permitting the gas, rising over the solution, to escape axially through the slot. In certain cases, a very small quantity of the solution likewise may pass through this orifice. This small quantity is sucked into the central shaft and retrieved in a closed receptable due to the accessory suction means of the mounted automatic device. Afterwards the slot 19 closes and the stopper—piston—valve resumes its function as a tight seal.

This means that the method provides the condition of a sterile solution in a cylindrical glass container closed at the bottom and being fire proof, under the total absence of gas as a result of the construction of the stopper—piston—valve.

After these operations, the reservoir is ready to be subjected to a final sterilization in an autoclave, where the solution is subjected to a temperature of 120° C. for a period of five minutes. The sterilization in the autoclave has to under sub-pressure in order to prevent any movements of the stopper and to preserve the seal of the slot.

The other components of the syringe define an injector. This injector is pre-assembled and intended to be connected to the reservoir. It may be sterilized initially in an autoclave or it may be radiosterilized. However, it may not be completely sterile when assembled with the reservoir. In such a case the autoclave sterilization takes place after finishing the product under the same conditions. This process applies to the assembly of the devices without liquid components.

FIG. 2 shows the syringe on completion of injection. In order to inject the medicinal substance, the hood 16 has to be removed by breaking the connection arms 28, then, without other steps, the operator pricks the patient and then exerts an axial pushing force on the bottom of the reservoir, which causes an increase of the pressure in the solution up to the predetermined threshold at which the shaft penetrates the slot in order to open the path for permitting the substance to flow along the conduit through the needle joined to this conduit towards the patient's perforated tissues.

When the reservoir is completely empty, an internal pad 32, provided at the open end of the reservoir, co-operates with an enlargement 33 situated at the base of the shaft 22 in order to lock the shaft to the reservoir and to prevent a re-use of the syringe.

Figure 3:
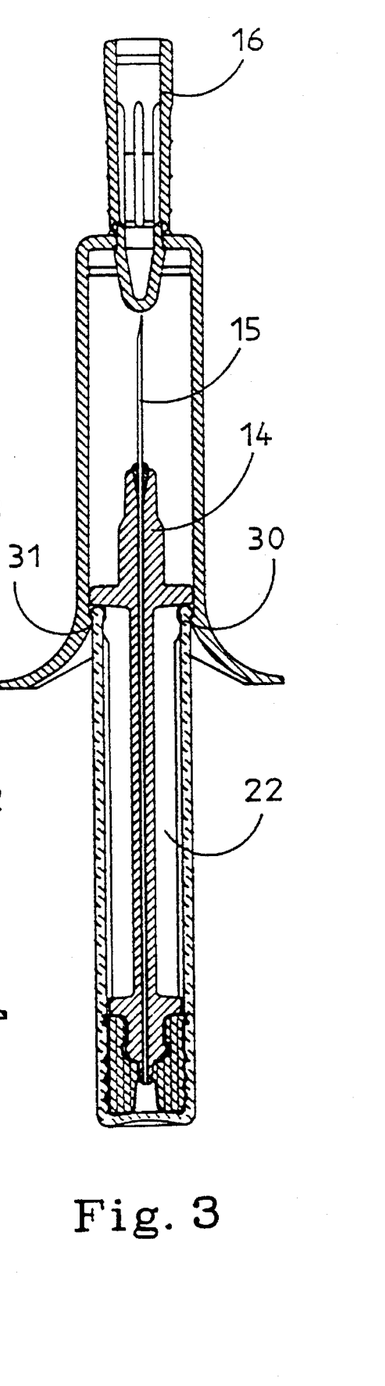
FIG. 3 shows the syringe of FIG. 1 with a neutralized needle after completion of use.

FIG. 3 shows how, due to this locking, the shaft 22 is brought towards the open end of the body, if the reservoir is retracted. The needle, which is connected to this shaft, is moved away into the interior of the body of the syringe to a position behind in which the external pad 30 co-operates with the neck 31. In this manner the needle is locked in position protected by the body. In addition to this, as is shown in the drawing, the tip of the protection hood 16 may be of an "arrow" design in order to be irreversibly clipped when the hood has been returned into the orifice of the body of the open syringe by ferrule 14 when the needle has been put away. This construction allows to neutralize the syringe after use and to prevent access to the soiled tip of the needle. It has to be noted that the storing away of the tip is done from behind the syringe. When the needle is placed within the body, accidental risks of pricking are excluded. The needle is not visible, and there is no risk when one places the hood over the opening of the body in order to block access to the needle.

Figure 4:
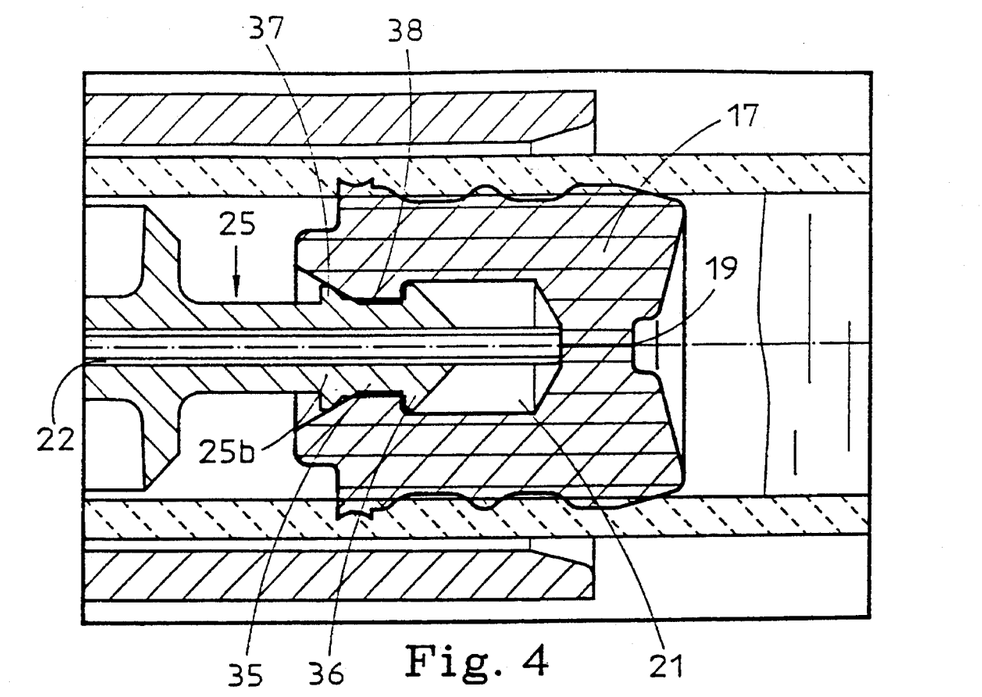
FIG. 4 shows an enlarged view of the stopper—piston—valve of the syringe according to the invention during storage.
Figure 5:
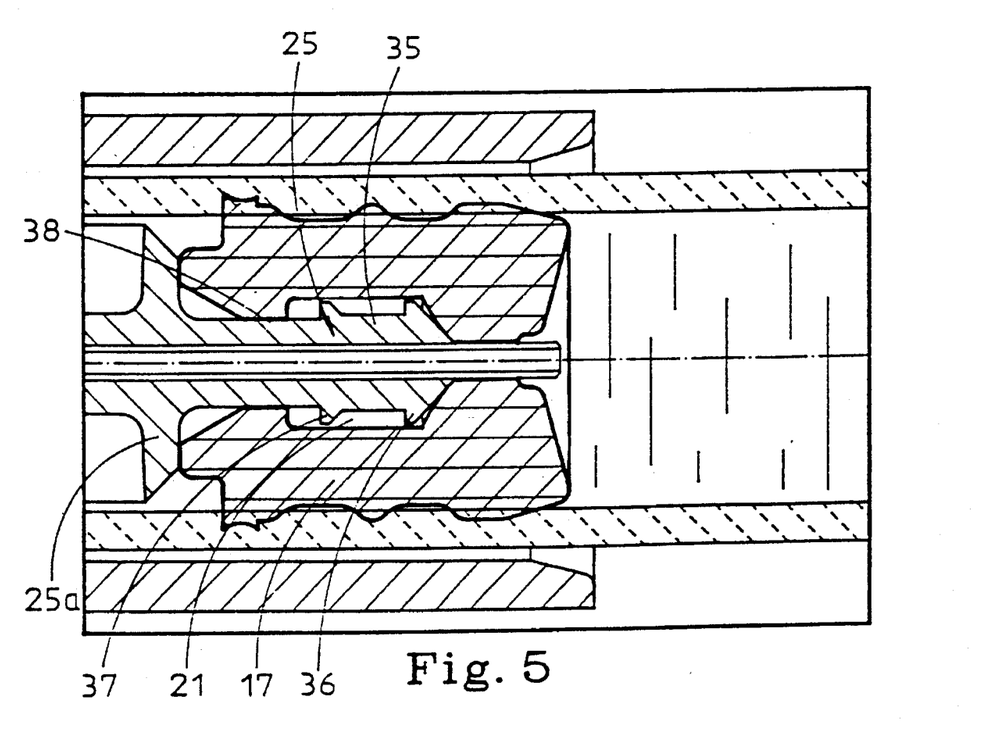
FIG. 5 shows a view of the syringe in accordance with the invention during use, the view being similar to that of FIG. 4.

FIGS. 4 and 5 show an enlarged view of the stopper—piston—valve 17, where the construction is substantially different from that of the stopper—piston —valve of the preceding figures. It will be noted that the clamping block 25 has a peripheral neck 35, defined by two rigid shoulders 36, 37, situated on both sides at this neck. This neck is adapted to receive an annular protuberance 38 provided in the central zone, in the downstream groove 21 of the stopper—piston—valve. The protuberance 38 is engaged during storage shown in FIG. 4, in the peripheral neck 35. During installation of the clamping block below the stopper—piston—valve, which may be made by means of a pushing member equipped with a spring, a first shoulder 36 compresses the resilient material of protuberance 38 of the stopper—piston—valve 17 so as to expand it. The second shoulder 37 arrives at an abutment to that protuberance when the first shoulder 36 is disconnected in order to come to the support of the front side of protuberance 38. To achieve this effect the resistance to the shoulder 36 has to be lower than that of the opposite shoulder 37. The shoulder 36 preferably has a section smaller than that of shoulder 37. The end of shaft 22 supports the slot 19, yet without engaging itself therein.

In return, in the condition represented by FIG. 5, the shaft 22 is engaged in the slot. The pressure exerted by the slot on the lips delimiting them, has caused it to open. The clamping block 25 is entirely lodged in the downstream groove 21 and the large part 25A of this block is in support and serves as a buttress to the stopper—piston—valve.

During storage, the tightness and the preservation of sterility are assured by the antibacterial barrier constituted by the lips of slot 19 and by the protuberance 38 and the shoulders 36 and 37. The shoulder 36 has a lower resistance to the passage of protuberance 38 than that of the shoulder 37, which fact allows a perfect mounting of the reservoir due to, the pressure exerted by defective resilience. The tightness obtained at this level, may be checked by a "blue bath" in under pressure and overpressure at about 0,25 bar during a period of 30 minutes according to the stipulations of pharmacopoeia.

The height of the slot 19 is relatively important, likewise the compression exerted by the lips. This is made possible by the fact that the opening is achieved by exerting a mechanical pushing force at the end of the shaft and by an overpressure exerted by a liquid. The resistance during testing by a "blue bath" is a demonstration of the efficiency of the system. No former system could meet such a test.

Resuction is possible with this syringe because the slot is kept open so that the shaft is introduced therein and the pad 37 gives support to protuberance 38. The displacement of the stopper—piston—valve and the reservoir triggers either a discharge or a suction according to the direction of displacement.

Figure 6:
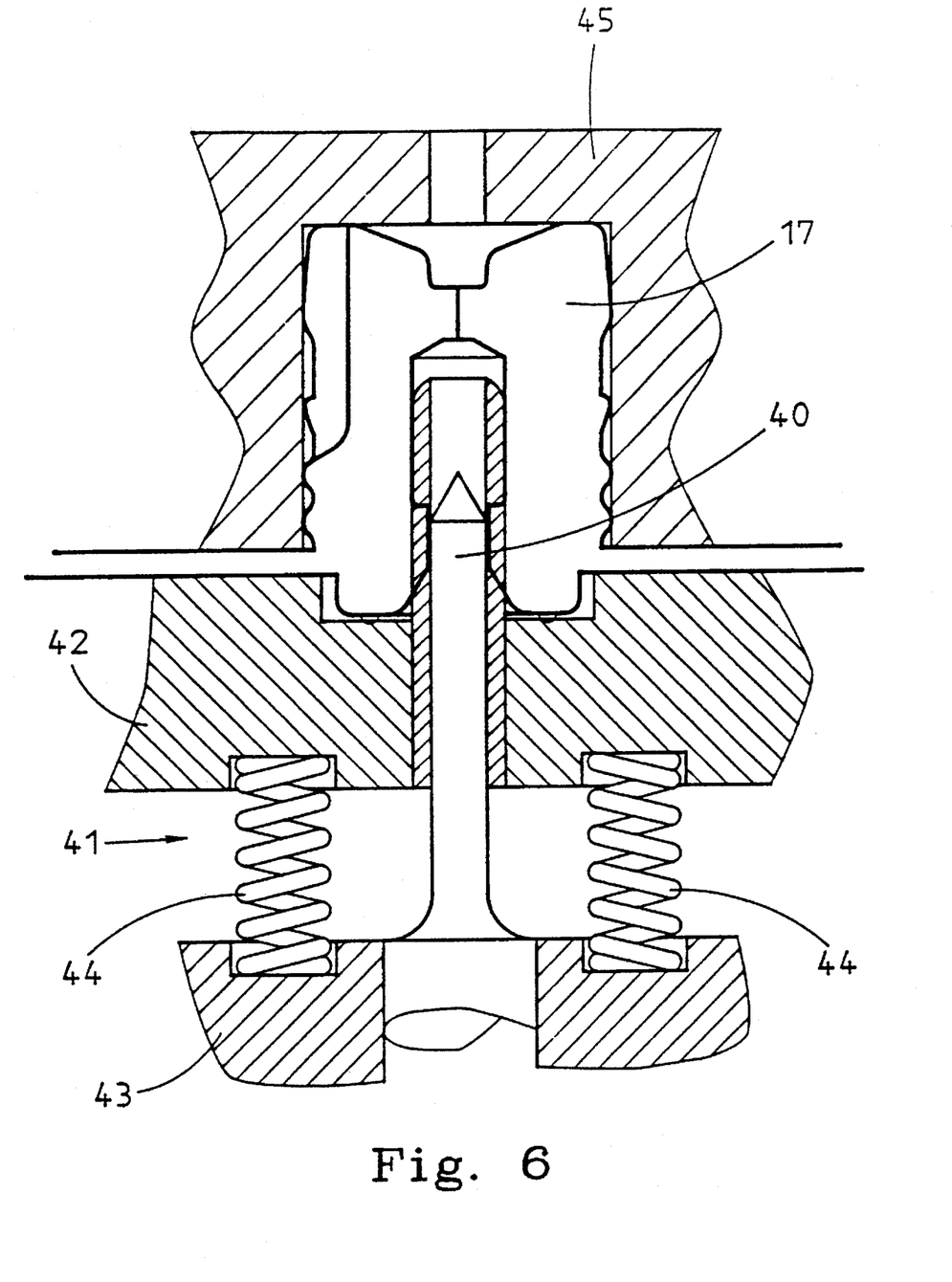
FIG. 6 shows a sectional view illustrating the steps of piercing the stopper—piston—valve.
Figure 7:
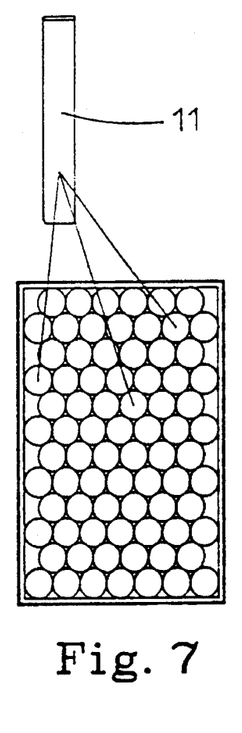
FIGS. 7 to 12 illustrate the procedure of refilling and of control of the reservoir of the syringe according to the invention.
Figure 8:
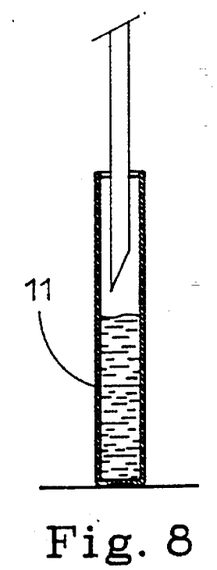
Figure 9:
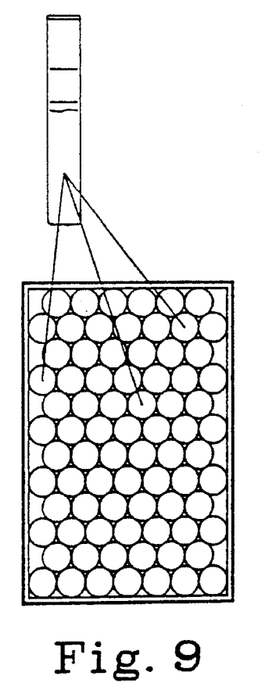
Figure 10:
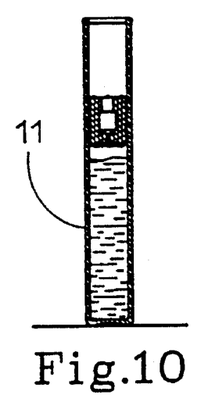
Figure 11:
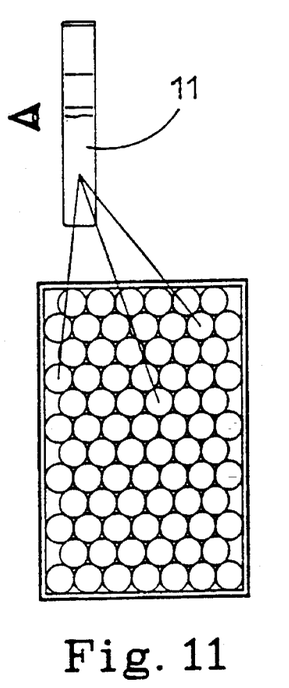
Figure 12:
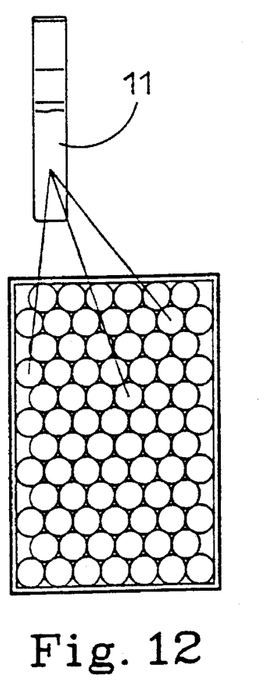

FIG. 6 shows an embodiment of a slot 19, which is perfectly centred. A piercing shaft mounted on a tool 41 composed of two pieces 42 and 43 and assembled by springs 44 ensures the piercing of stopper—piston—valve 17 kept in place in an appropriate cavity of a support 45.

FIGS. 7 to 12 illustrate phases of rinsing—siliconisation—sterilization (FIG. 7), refilling (FIG. 8), installation in the magazine in order to transfer (FIG. 9), piercing (FIG. 10), visual control (FIG. 11) and installation in the magazine (FIG. 12) of reservoir 11 for sterilisation in an autoclave and overpressure.

Figure 13:
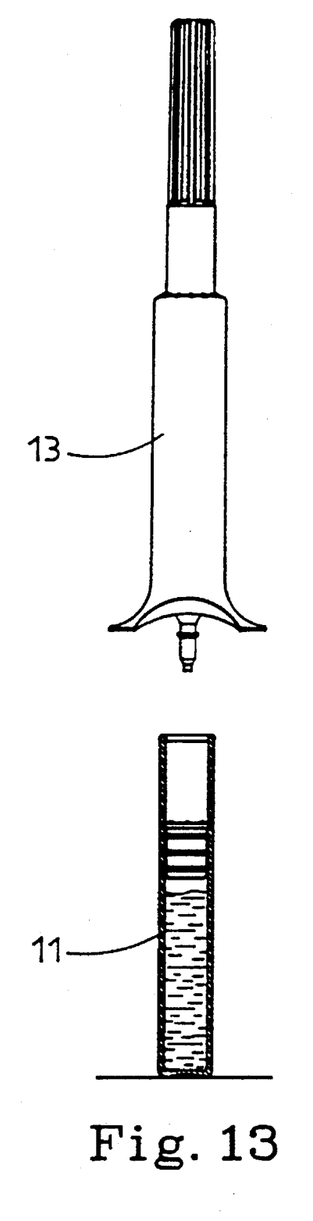
FIGS. 13 to 15 show the phases of assembly, control and labelling of both sub-assemblies constituting the syringe of the invention.

FIG. 13 shows the assembly of two sub-units, being the reservoir 11 and the body 13 which constitute the syringe 10.

Figure 14:
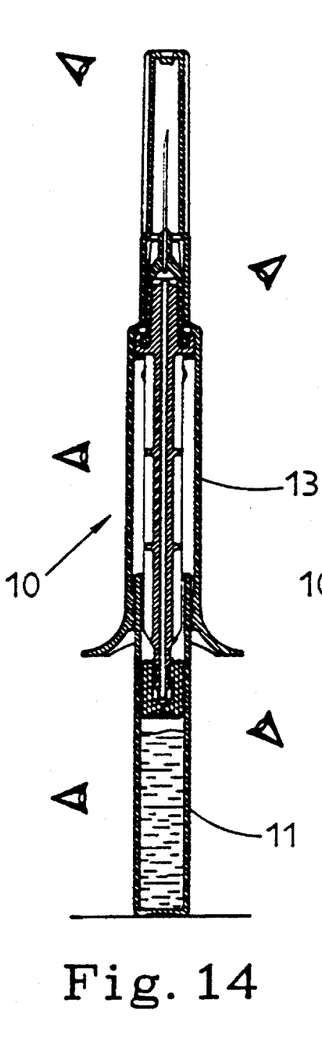
Figure 15:
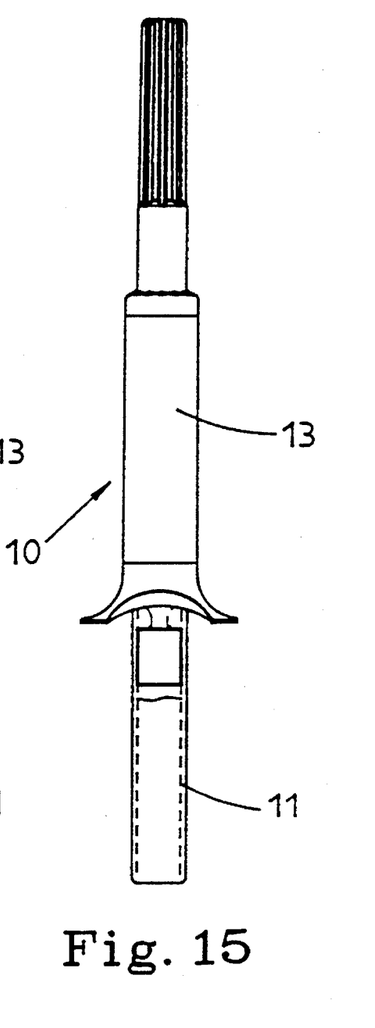

FIG. 14 shows the final control phase of the syringe 10 and FIG. 15 shows the labelling of the syringe.

Figure 16:
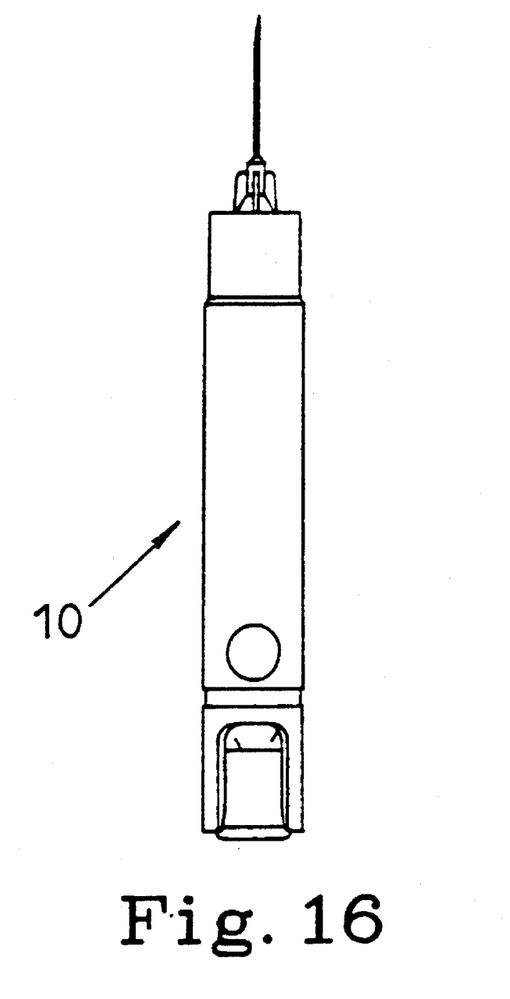
FIGS. 16 and 17 illustrate two phases of use of the syringe of the invention.
Figure 17:
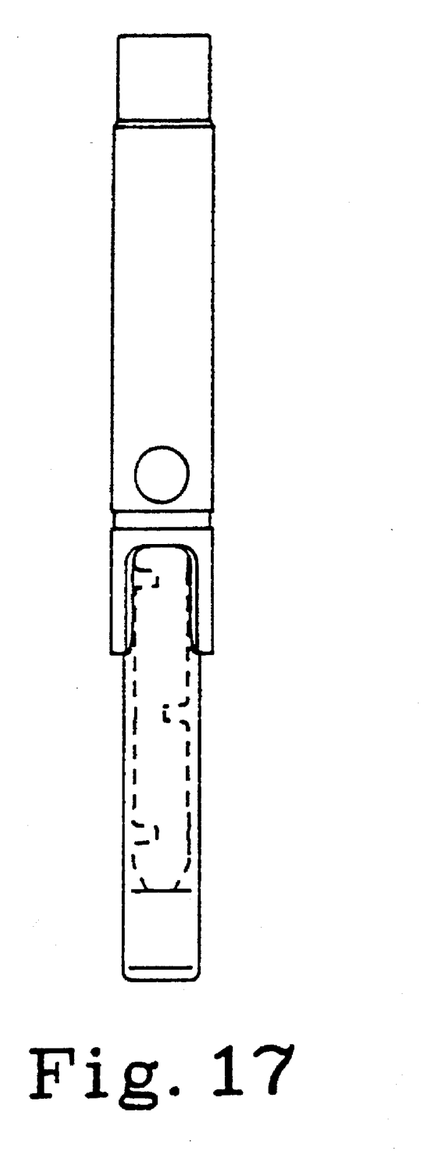
Figure 18:
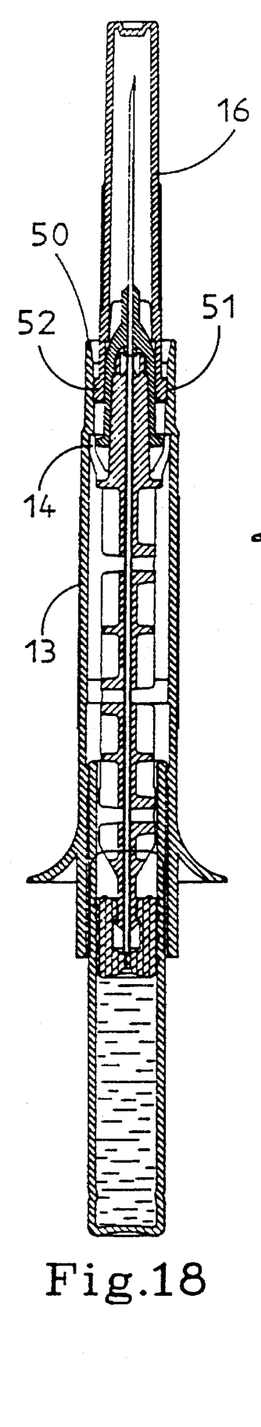
FIGS. 18 to 21 are views representing a variation embodiment of the syringe of the invention in different phases of use.
Figure 19:
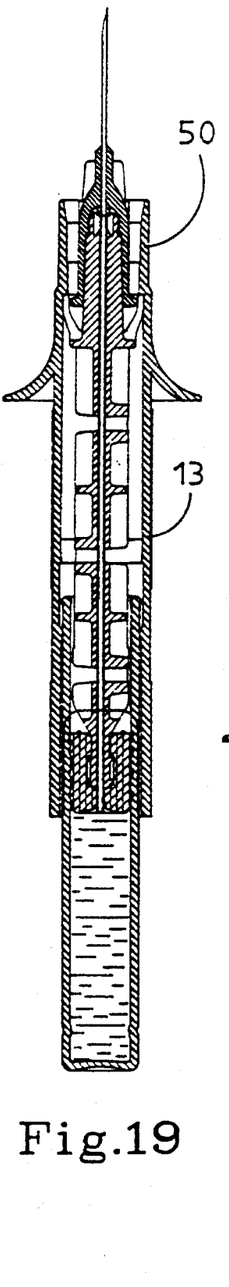
Figure 20:
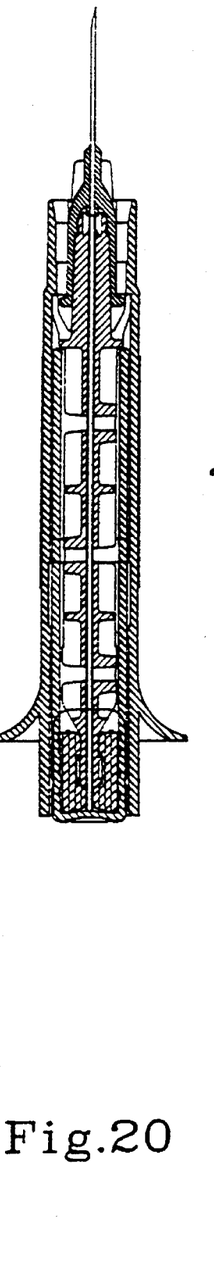

FIG. 16 shows the syringe on completion of the injection, and FIG. 17 shows when the needle has been retracted.

Figure 21:
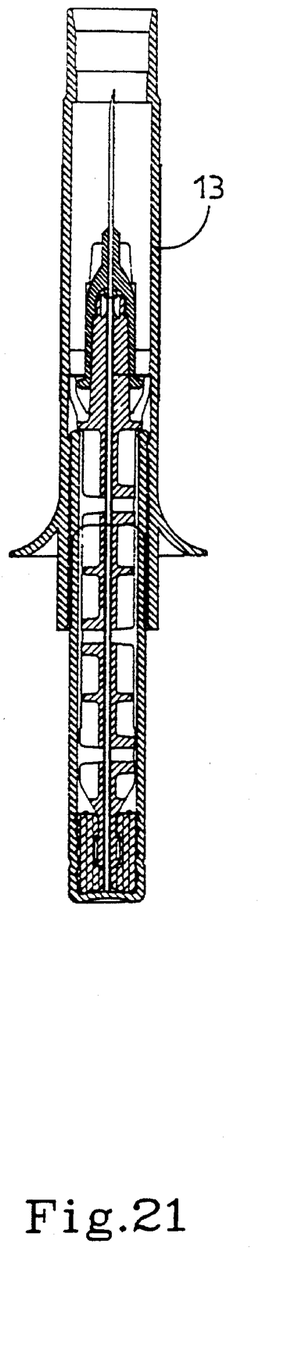

FIGS. 18 to 21 show a different embodiment of the syringe, respectively during storage (FIG. 18), during use (FIG. 19), on completion of injection (FIG. 20) and after retraction of the needle (FIG. 21). It will be noted that the body 13 is provided with a skirt 50 which extends to the ferrule carrying needle 14. A zone of tightness 51 is defined by the support to the skirt 50 of pad 52 provided at the base of protection hood 16 of the needle.

Figure 22:
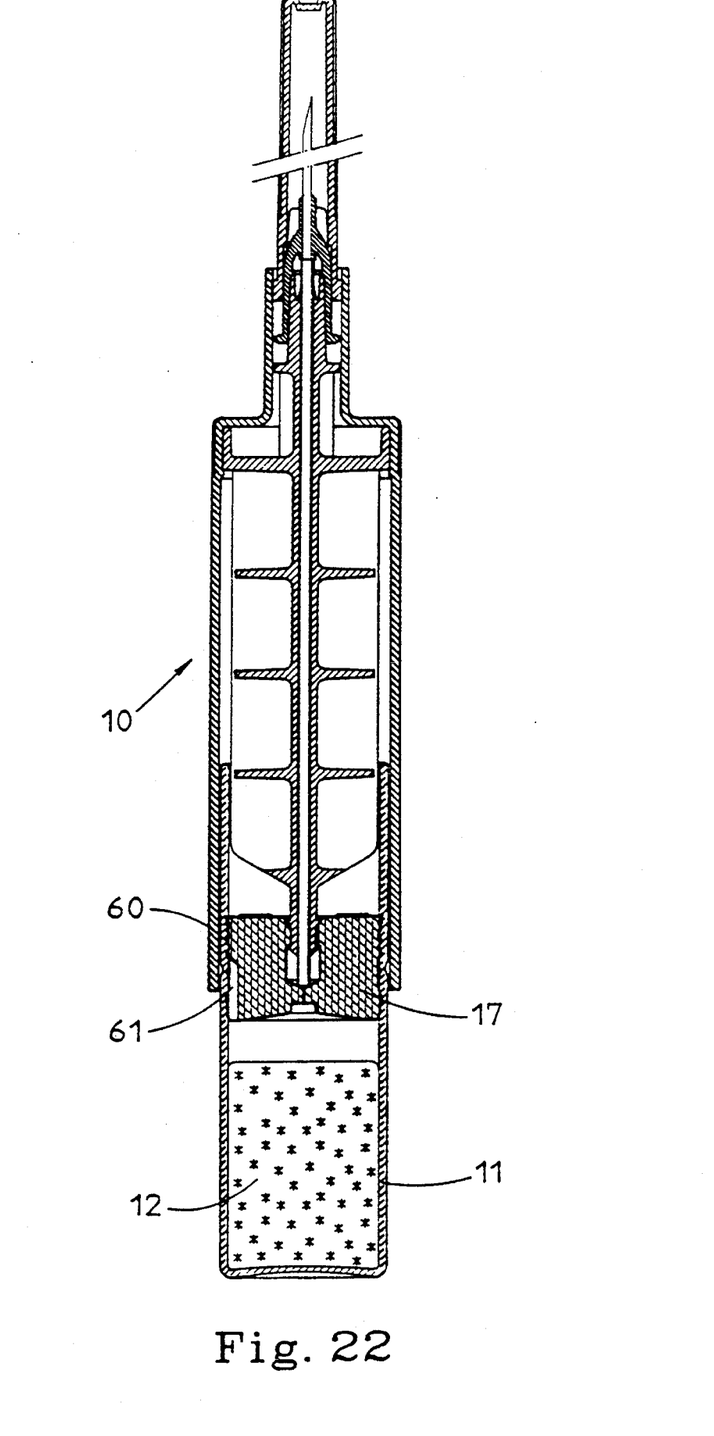
FIG. 22 shows a syringe containing a solid or pasty substance.

FIG. 22 shows a syringe 10 of which the reservoir contains a dry substance 12 which may be a powder, a lyophilisate or a viscose material requiring a dilution prior to injection.

The stopper—piston—valve 17 has at least one shoulder 60, which provides perfect tightness. This shoulder is used when the substance is stored in the groove or absorbs the carbonic anhydride during storage in order to give support to an internal shoulder 61 of the reservoir 11.

Figure 23:
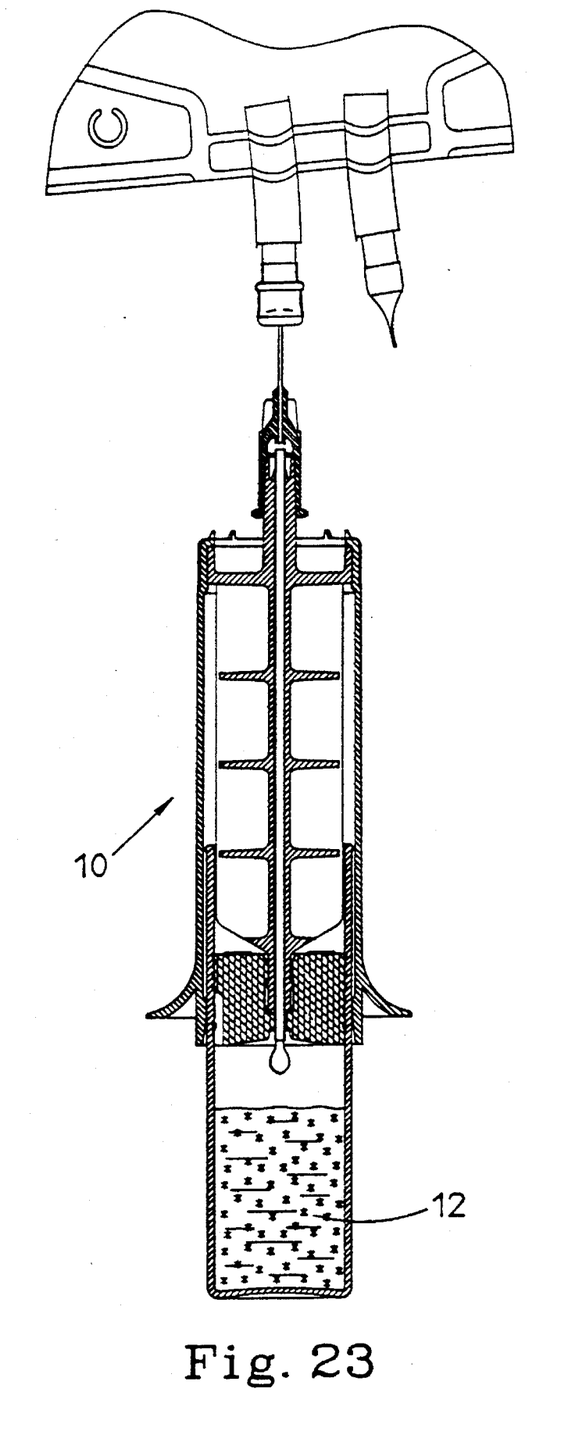
FIG. 23 shows the phase of dilution or dissolution of the substance contained in the syringe of FIG. 22.

FIG. 23 shows a syringe 10 connected to a bag containing a dilutant or a solvent intented to dilute or dissolve a substance 12. After such dilution or dissolution the contents may be transferred to the bag, to a different bag, to a bottle or the like.

Figure 24:
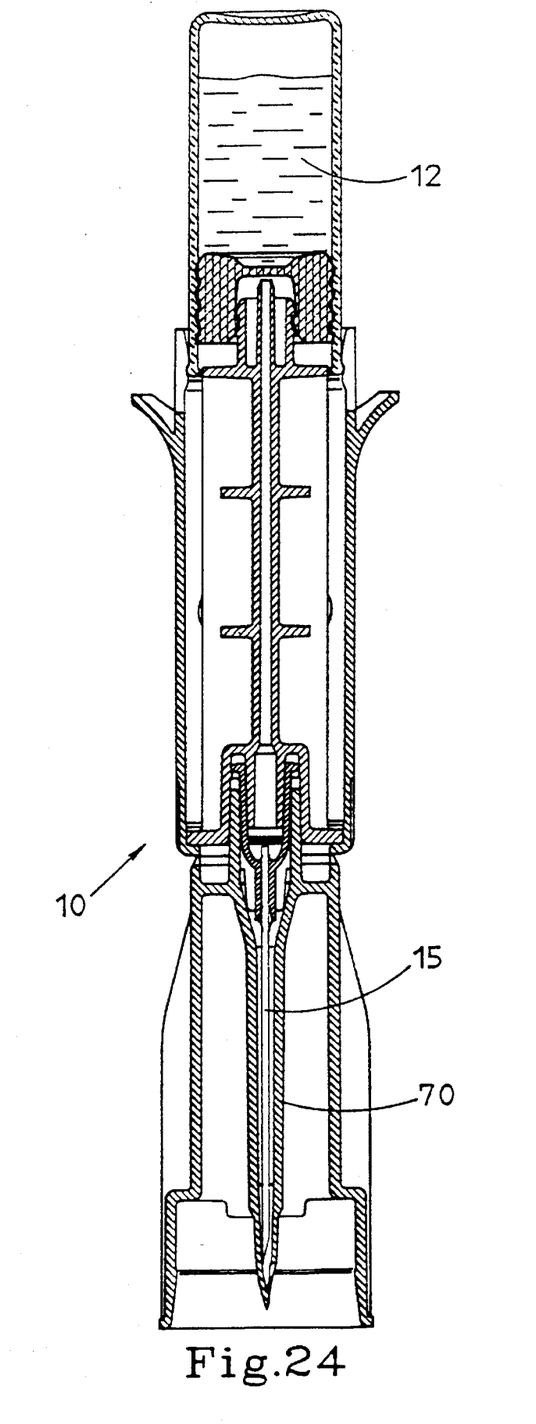
FIG. 24 shows a variation embodiment of a syringe according to the invention.

FIG. 24 shows a syringe 10 provided with a needle 15. Initially this needle is protected by a perforation device 70 intended to pierce the seal of a bottle in order to permit a mixture of a substance 12 with a component procured from a different container. After the transfer of this component to the reservoir, the perforation device is separated from the syringe which then becomes a syringe identical or similar to that of FIG. 1.

I claim:

1. A prefilled syringe for storing and transferring of a sterile liquid medical substance, said prefilled syringe comprising a glass reservoir having a closed bottom and being closed at an open end opposite to the closed bottom by a stopper—piston—valve which is axially slidable within said reservoir, said reservoir being axially movable within a hollow cylindrical body and having a central shaft provided with an axial conduit which communicates with a needle fixed to a proximal end of the body opposite to said reservoir, said shaft being provided with connecting means for allowing a secure connection to said stopper—piston—valve, said connecting means including a clamping block (25) provided with a peripheral neck (35) adapted to receive a protuberance (38) of said stopper—piston—valve during a storage phase of the syringe and said stopper—piston—valve having a central cavity for receiving said clamping block during a use phase of the syringe, wherein said stopper—piston—valve has a pre-cut slot defined by two lips and disposed in prolongation of said central cavity, said slot has a sufficiently large height such that said lips are sufficiently compressed laterally to completely sealingly close said slot during said storage phase and, during use, to ensure a completely tight seal between said stopper—piston—valve and an exterior surface of the end of said shaft extending through said slot during said use phase so that the sterile liquid medical substance only flows through said tube along said axial conduit and the sterile liquid medical substance does not flow between the exterior surface of said tube and said lips of said stopper—piston—valve.

2. A syringe according to claim 1, wherein said shaft (22) is integral with a flange (24) adapted to bear on an inner surface of a distal end of said hollow cylindrical body (13).

3. A syringe according to claim 1, wherein said clamping block (25) has a wide portion (25a) with a diameter which is substantially equal to an inner diameter of said hollow cylindrical body (13) to ensure centering of said shaft within said body.

4. A syringe according to claim 1, wherein said clamping block (25) has a narrow portion (25b) provided with two shoulders (36 and 37) disposed on both sides of said peripheral neck (35).

5. A syringe according to claim 4, wherein a first of said shoulders (36) is adapted to offer less resistance to compression provided by said protuberance (38) than that offered by a second of said shoulders (37).

6. A syringe according to claim 5, wherein said first shoulder (36) has a smaller cross-section than said second shoulder (37).

7. A syringe according to claim 1, wherein said reservoir (11) has an external shoulder (30) which co-operates with a neck (31) provided at a free end of said body (13).

8. A syringe according to claim 1, wherein said reservoir (11) has an internal shoulder (32) which co-operates with an enlargement (33) located at a base of said shaft (22) once the sterile liquid medical substance has been completely discharged.

9. A syringe according to claim 1, wherein said pre-cut slot is centered with respect to said central cavity of said stopper—piston—valve.

10. A syringe according to claim 1, wherein the sufficiently large height of said slot is such that when a leading portion of said tube is completely accommodated with a first elongate portion of said slot proximate said clamping block, a second elongate portion of said slot proximate said reservoir still remains closed to prevent the flow of the sterile liquid medical substance through said tube until said tube is completely inserted through both the first and second elongate portions of said slot.

11. A syringe according to claim 1, wherein the sufficiently large height of said slot is such that said lips are biased substantially radially outward by said tube during penetration of said tube into said slot.

* * * * *